United States Patent [19]
Kanzaki et al.

[11] Patent Number: 5,693,504
[45] Date of Patent: Dec. 2, 1997

[54] MICROORGANISM RESISTANT TO NICOTINIC ACID ANALOGUE AND PRODUCTION OF BIOTIN

[75] Inventors: Naoyuki Kanzaki, Ibaraki; Hiroyuki Kimura, Sakai; Junji Matsui, Suita; Kazuo Nakahama, Nagaokakyo; Ohji Ifuku, Yokohama, all of Japan

[73] Assignees: Takeda Chemical Industries, Ltd., Osaka; Shiseido Company, Limited, Tokyo, both of Japan

[21] Appl. No.: 572,057

[22] Filed: Dec. 14, 1995

[30] Foreign Application Priority Data

Dec. 15, 1994 [JP] Japan .................. 6-311778

[51] Int. Cl.[6] .................. C12N 1/21; C12N 5/10; C12P 17/18
[52] U.S. Cl. .................. 435/119; 435/252.3; 435/252.33; 435/325
[58] Field of Search .................. 435/118, 240.2, 435/252.3, 252.31, 252.33, 119, 325

[56] References Cited

U.S. PATENT DOCUMENTS 5,374,554 12/1994 Komatsubara et al. .......... 435/252.3

FOREIGN PATENT DOCUMENTS

| 61-149091 | 7/1986 | Japan . |
| 2-027980 | 1/1990 | Japan . |
| 4-011894 | 1/1992 | Japan . |
| 5-199867 | 8/1993 | Japan . |

OTHER PUBLICATIONS

Tritz, in Escherichia coli & Salmonella typhimurium, Cellular and Molecular Biology, Neidhardt et al. (eds.), Am. Soc. Microbiol., Washington, DC, pp. 557–563, 1987.

McGraw–Hill Dictionary of Chemical Terms, Sybil P. Parker (ed.), McGraw–Hill Book Co., New York, NY, 1985.

Fujisawa et al., "Biotin Production by bioB Transformants of a *Bacillus sphaericus* Mutant Resistant to 1–(2'–Thenoyl)–3,3,3–trifluoroacetone, an Electron Transport Inhibitor", Biosci. Biotech. Biochem., vol. 58 (6), pp. 1018–1022, 1994.

Sakurai et al., "Improvement of a d–biotin–hyperproducing recombinant strain of *Serratia marcescens*" Journal of Biotechnology, vol. 36 pp. 63–73, 1994.

Sakurai et al., "Construction of a Biotin–Overproducing Strain of *Serratia marcescens*" Applied and Environmental Microbiology, vol. 59, No. 9, pp. 2857–2863, Sep. 1993.

*Primary Examiner*—Eric Grives
*Attorney, Agent, or Firm*—Wenderoth, Lind & Ponac

[57] ABSTRACT

A microorganism resistant to a nicotinic acid analogue, which has a plasmid containing part or whole of a biotin operon; and a process for producing biotin, which comprises culturing a microorganism described above in a medium to produce and accumulate biotin in the medium, and collecting biotin.

4 Claims, 2 Drawing Sheets

MICROORGANISM RESISTANT TO NICOTINIC ACID ANALOGUE AND PRODUCTION OF BIOTIN

BACKGROUND OF THE INVENTION

1. Field of the Invention

The present invention relates to a novel microorganism resistant to a nicotinic acid analogue and a process for producing biotin using the microorganism. The biotin obtainable by the invention can be used as a raw material for medicaments or cosmetics, feed additives, etc.

2. Description of Related Art

Biotin (vitamin H) is a kind of vitamin B and is related to fatty acid synthesis or saccharide metabolism as a coenzyme of a carboxylase. About 10 tons of biotin is produced by chemical synthesis processes every year for use as a raw material for medicaments or cosmetics, feed additives, etc. However, because these processes are complicated, biotin is very expensive. On the other hand, biotin production by fermentation processes has been studied for a long time. The fermentation processes have not become practical because their productivity is low.

Biotin production using gene manipulation techniques has been expected to provide inexpensive biotin. Some microorganisms modified by gene engineering techniques have been used for biotin production. For example, microorganisms belonging to the genus Escherichia such as a strain resistant to α-dehydrobiotin disclosed in e.g. JP-A 61-149091 are known as the modified microorganisms for the biotin production. Other known modified microorganisms for the biotin production include microorganisms belonging to the genus Bacillus modified by transforming *Bacillus sphaericus* and then providing resistance to thenoyltrifluoroacetone (JP-A 4-11894), microorganisms belonging to the genus Serratia modified by providing *Serratia marcescens* SB411 with ethionine-resistance followed by S-aminoethylcysteine-resistance and then transforming the resulting microorganism with a recombinant plasmid containing a biotin gene fragment (JP-A 5-199867), and transformants of *Serratia marcescens* SB411 provided with resistance to actithiazic acid, a compound having biotin-like structure, or resistance to 5-(2-thienyl)-n-valeric acid (JP-A 2-27980).

However, the prior art processes for producing biotin are unsatisfactory for the industrial production of biotin. There is still a need for a process for producing biotin having increased biotin productivity.

The main object of the present invention is to provide a microorganism which can produce biotin in high yield.

Another object of the present invention is to provide a process for producing biotin using the above microorganism.

These objects as well as other objects and advantages of the present invention will become apparent to those skilled in the art from the following description with reference to the accompanying drawings.

SUMMARY OF THE INVENTION

The present inventors have paid attention to the fact that reduced nicotinamide adenine dinucleotide phosphate (NADPH) is essential for the reaction from dethiobiotin to biotin that is a final step of biotin biosynthesis (Biosci. Biotech. Biochem., vol. 56, p. 1780 (1992), etc.). The inventors expected that enhancing NADPH productivity of biotin-producing microorganisms would improve biotin accumulation.

The present inventors have isolated a strain resistant to a nicotinic acid analogue from a biotin-producing microorganism to obtain a strain with significantly increased biotin accumulation. After further studies based on this finding, the present invention has been completed.

The present invention provides a microorganism resistant to a nicotinic acid analogue, which has a plasmid containing part or whole of a biotin operon.

The present invention also provides a process for producing biotin, which comprises culturing a microorganism described above in a medium to produce and accumulate biotin in the medium, and collecting biotin.

DETAILED DESCRIPTION OF THE INVENTION

The nicotinic acid analogues include, for example, 6-aminonicotinamide, isonicotinic acid hydrazide, 3-pyridinesulfonic acid, 3-pyridylacetic acid, 2-hydroxynicotinic acid, pyrazinecarboxylic acid, methyl nicotinate, 3-aminobenzamide, 6-methylnicotinamide, pyrazinamide, and 6-aminonicotinic acid. In particular, 6-aminonicotinamide is preferred.

Figure 1:
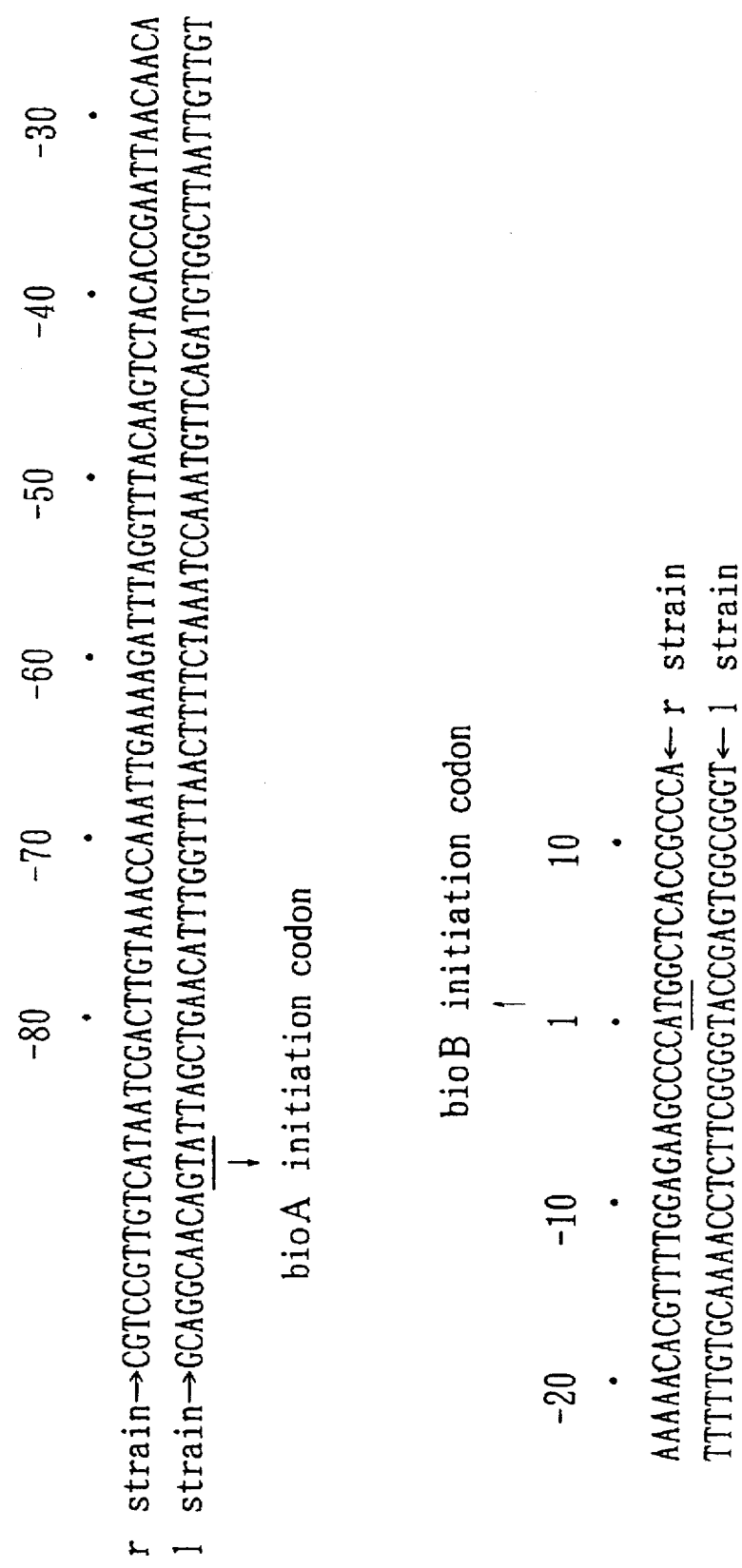
FIG. 1 shows a regulatory region of the biotin operon and a base sequence near the bio B initiation codon.

The biotin operons include, for example, biotin operons derived from microorganisms belonging to the genera Escherichia, Bacillus, and Serratia. The biotin operons derived from microorganisms belonging to the genus Escherichia include biotin operons derived from *Escherichia coli* (JP-A 61-202686, etc.). The five genes bioA, bioB, bioC and bioD that are involved in biotin biosynthesis are encoded in the biotin operon. In the invention, part of the biotin operon may be modified. The modified biotin operons include, for example, those wherein at least one base pair of either the base sequence of the regulatory region of the biotin operon or the base sequence near the bioB initiation codon of *Escherichia coli* is mutated as compared with the wild type. The regulatory region of the biotin operon is the base sequence shown in Sequence Listing 1 that is a base sequence of r-strand between bioA and bioB, specifically the base sequence of the region from bp (base pair) −1 to bp −86 shown in FIG. 1 when A of the bio B initiation codon ATG is considered bp 1. The base sequence near the bioB initiation codon is the region from bp 1 to bp 6 when A of the bioB initiation codon ATG is considered bp 1. Specifically, at least one GC pair of upstream bp −53 and bp −5 and downstream bp 4 when A of the bioB initiation codon ATG is considered bp 1 is mutated to an AT pair (JP-A 5-219956).

The plasmid to be used in the invention is a plasmid which can be carried by microorganisms belonging to the genus Escherichia, Bacillus or Serratia and the gene of which can be expressed. The plasmid is preferably a plasmid carried by microorganisms belonging to the genus Escherichia. Examples of the plasmids include pXBA312 (derived from *Escherichia coli* DRK-3323 (pXBA312)(FERM BP-2117), JP-A 2-502065), pXBRP319 (derived from *Escherichia coli* MM44/pXBRP319 (IFO 15721, FERM BP-4724), see Example 1 below) and derivatives thereof.

The microorganism of the invention can produce and accumulate biotin. Examples thereof include microorganisms belonging to the genus Escherichia, Bacillus or Serratia, etc. The microorganism is preferably a microorganism belonging to the genus Escherichia such as *Escherichia coli*, preferably *Escherichia coli* ANA91/pXBRP319 (IFO 15771, FERM BP-4928) obtained in Example 1 below.

The microorganism resistant to a nicotinic acid analogue having a plasmid containing part or whole of the biotin operon is preferably a microorganism resistant to nicotinic acid analogue transformed with a plasmid containing part or whole of the biotin operon.

The microorganism of the invention can be obtained, for example, by providing a parent strain of a microorganism with resistance to a nicotinic acid analogue and introducing a plasmid containing part or whole of the biotin operon into the resulting strain resistant to the nicotinic acid analogue. The microorganism of the invention can also be obtained by introducing a plasmid containing part or whole of the biotin operon into a parent strain of a microorganism and providing the resulting microorganism with resistance to a nicotinic acid analogue. Alternatively, the microorganism can be obtained by providing with resistance to a nicotinic acid analogue a parent strain of a microorganism carrying a plasmid containing part or whole of the biotin operon.

As the parent strains, any microorganisms can be used in the invention so long as they can produce and accumulate biotin. Examples of the microorganisms include microorganisms belonging to the genera Escherichia, Bacillus and Serratia. The microorganisms belonging to the genus Escherichia include microorganisms belonging to *Escherichia coli*, such as *Escherichia coli* IFO 14410, *Escherichia coli* W-3110 (IFO 12713) and its derivative strain *Escherichia coli* DR-85 (JP-A 61-202686), *Escherichia coli* DR-332 (JP-A 62-155081), *Escherichia coli* DRK-3323 (JP-A 2-502065), *Escherichia coli* BM4062 (JP-A 64-500081), *Escherichia coli* MS10/pXBRP319 (IFO 15570, FERM BP-4927) obtained in Example 1 below. The above *Escherichia coli* IFO 14410 and *Escherichia coli* IFO 12713 are known strains listed in List of Cultures, 9th edition (1992) (published by IFO) and available from institute for Fermentation, Osaka, Japan.

The microorganisms belonging to the genus Bacillus include, for example, microorganisms belonging to *Bacillus sphaericus*. Specific examples thereof include *Bacillus sphaericus* IFO 3525 and its derivative strain *Bacillus sphaericus* NZ-8802 (JP-A 4-11894). The above *Bacillus sphaericus* IFO 3525 is a known strain listed in List of Cultures, 9th edition (1992) (published by IFO) and available from Institute for Fermentation, Osaka, Japan.

The microorganisms belonging to the genus Serratia include microorganisms belonging to *Serratia marcescens*. Specific examples thereof include *Serratia marcescens* Sn 41 and its derivative strain *Serratia marcescens* TA5024 (JP-A 2-27980), *Serratia marcescens* SB411 and its derivative strain *Serratia marcescens* ET2, *Serratia marcescens* ETA23 (JP-A 5-199867), etc.

The above microorganisms can be used as such or as mutants thereof. When the microorganisms contain no plasmid containing part or whole of the biotin operon, if necessary, a plasmid containing part or whole of the biotin operon is introduced into the microorganisms at a later step.

The strains resistant to a nicotinic acid analogue can be obtained by per se known methods such as treatment with chemicals (e.g., N-methyl-N'-nitro-N-nitrosoguanidine abbreviated as NTG), and ultraviolet irradiation.

Then, a suspension of the resulting mutant cells is inoculated in a culture medium (e.g., agar plate culture medium) containing a nicotinic acid analogue in an appropriate concentration, e.g., a concentration which does not allow the growth of the parent strain. The grown colonies are isolated to obtain the strain resistant to the nicotinic acid analogue.

The nicotinic acid analogue-resistant strain obtained in the above method is cultured, and the amount of biotin in the culture supernatant is determined to select microorganisms which can accumulate increased amount of biotin.

The plasmid containing part or whole of the biotin operon can be introduced into the microorganism by per se known methods. The plasmid containing part or whole of the biotin operon can be constructed by per se known methods, for example, by DNA cleavage with a restriction enzyme followed by DNA linkage with T4DNA ligase (Molecular Cloning, A laboratory Manual, Cold Spring Harbor Laboratory, 1982).

The host cell can be transformed with the above plasmid by per se known methods. For example, when the host is a bacterium belonging to the genus Escherichia, the host can be transformed by the method described in Molecular Cloning, A Laboratory Manual, Cold Spring Harbor Laboratory, 1982.

The microorganism of the invention obtained in the above method is cultured in a medium to produce biotin in the medium.

The medium used for culture in the invention may be liquid or solid so long as it contains nutrition sources that the microorganisms to be used can utilize. For large scale culture, liquid media are preferably used. The medium contains assimilable carbon sources, assimilable nitrogen sources, inorganic materials, trace nutrients, etc. The carbon sources include glucose, lactose, sucrose, maltose, dextrin, starch, mannitol, sorbitol, glycerol, fats and oils (e.g., soybean oil, olive oil, bran oil, sesame oil, lard oil, chicken oil), and various fatty acids (e.g., lauric acid, myristic acid, palmitic acid, stearic acid, oleic acid). The nitrogen sources include meat extract, yeast extract, dried yeast, soybean flour, defatted soybean flour, corn steep liquor, peptone, cottonseed oil, blackstrap molasses, urea, thiourea, ammonia, and ammonium salts (e.g., ammonium sulfate, ammonium chloride, ammonium nitrate, ammonium acetate). In addition, salts including sodium, potassium, calcium, magnesium, etc., salts with metals such as iron, manganese, zinc, cobalt, nickel, etc., salts of inorganic acids such as phosphoric acid, boric acid, etc., salts of organic acids such as acetic acid, propionic acid, etc., can appropriately be used. In addition, amino acids (e.g., glutamic acid, aspartic acid, alanine, lysine, valine, methionine, proline), peptide (e.g., dipeptide, tripeptide), vitamins (e.g., vitamins $B_1$, $B_2$, $B_{12}$, C, nicotinic acid), nucleic acids (e.g., purine, pyrimidine and derivatives thereof), etc., can also be used. In order to control the pH in the medium, inorganic or organic acids, alkalis, etc., can be added. Appropriate amounts of oils and fats, sufactants, etc., can be used as antifoaming agents. The pH of the medium is preferably about 4 to 10, more preferably about 6 to 9.

The culture is any one of stationary culture, shaking culture, and aerobic and agitating culture. Aerobic and agitating culture is preferred for large scale culture. The temperature for culture is about 15° to 37° C., preferably about 30° to 37° C. The culture time varies with the culture conditions, but is normally about 1 to 10 days, preferably about 2 to 4 days.

The culture is conducted by per se known methods such as batch culture, and fed-batch culture.

The resulting culture broth is centrifuged, and the amount of biotin accumulated in the supernatant is determined by per se known methods such as bioassay using *Lactobacillus plantarum* as a test microorganism (The Vitamins, vol. 7, p. 303 (1967); Vitamins, Experimental Procedures (II), p. 475, edited by Japan Vitamin Society (1985); etc.).

The microorganism is cultured by the above method to produce and accumulate biotin in the culture, and then biotin is collected from the culture. Because the biotin thus produced is present mainly in the culture filtrate, it is advantageous to separate the culture to obtain the culture filtrate and cells by per se known methods (e.g., filtration, centrifugation), and separate and purify biotin from the resulting filtrate. Alternatively, biotin can be purified directly from the culture broth.

The separation and purification can be carried out by per se known methods using difference in solubility in an appropriate solvent, precipitation from a solution, difference in precipitation rates, difference in various absorbance affinity, ion-exchange chromatography using ion-exchangers, concentration under reduced pressure, lyophilization, crystallization, recrystallization, drying, etc. These techniques can be used alone or in an appropriate order of their combination.

Biotin obtained by the invention can be used as raw materials for medicaments, cosmetics, etc., feed additives, etc.

The microorganism of the invention has high biotin productivity. Culture of this microorganism can produce a large amount of biotin.

The following examples further illustrate the invention in detail, but are not to be construed to limit the scope of the invention. All the percents (%) regarding the medium is W/V percents (W/V %).

*Escherichia coli* MS10/pXBRP319 and *Escherichia coli* ANA91/pXBRP319 have been deposited at Institute for Fermentation, Osaka, Japan (IFO) under the Accession Numbers IFO 15770 and IFO 15771 since Dec. 2, 1994, respectively, and at National Institute of Bioscience and Human-Technology, Agency of Industrial Science and Technology, Tsukuba, Japan under the Accession Numbers FERM BP-4927 and FERM BP-4928 since Dec. 12, 1994, respectively.

EXAMPLE 1

Figure 2:
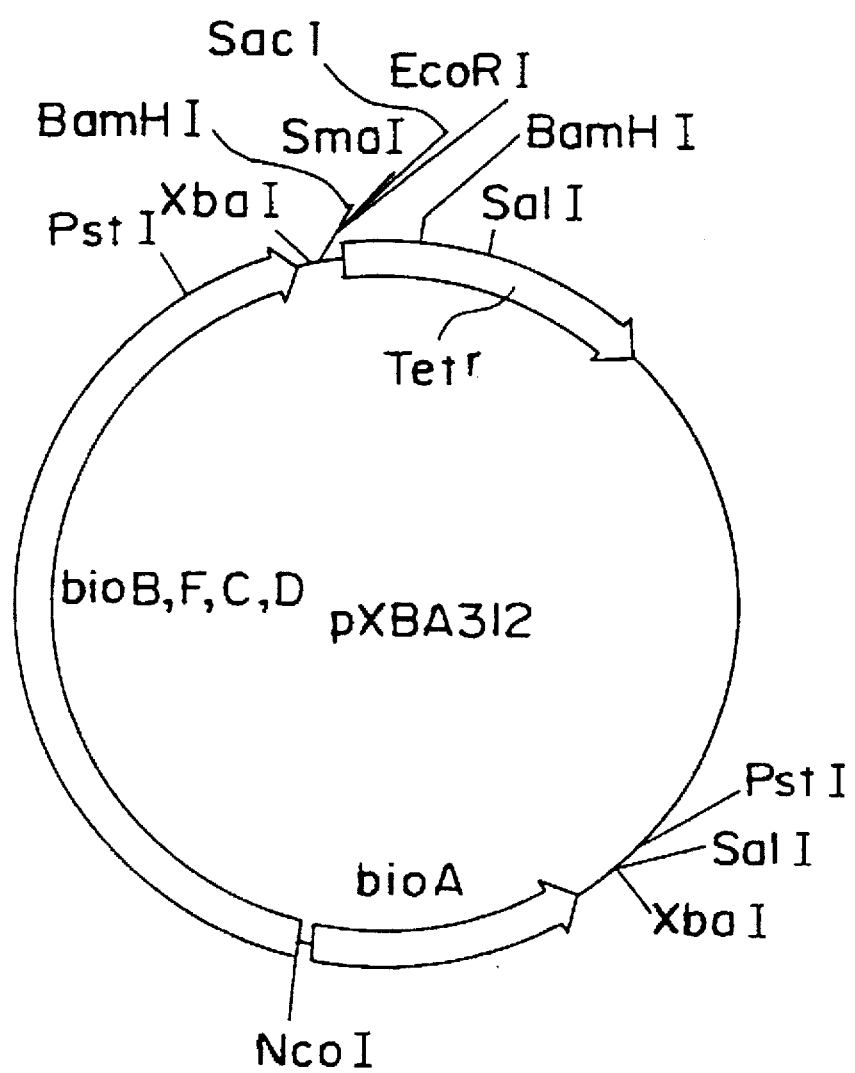
FIG. 2 is a restriction map of DNA of plasmid pXBA312.

(1) Plasmid pXBA 312 (see FIG. 2) isolated from *Escherichia coli* DRK-3323/pXBA 312 (FERM BP-2117) (JP-A 2-502065) was cleaved with the restriction enzyme EcoRI, partially digested with PstI, and subjected to agarose gel electrophoresis and electroelution to isolate an EcoRI-PstI fragment (6.0 Kbp) containing the full-length biotin operon. The resulting EcoRI-PstI fragment of pXBA 312 was ligated with an EcoRI-PstI fragment (3.6 Kbp) of plasmid pBR 322 to obtain plasmid pXBA 319.

Plasmid pMW 119 (Nippon Gene, Japan) was cleaved with the restriction enzymes AatII and AvaI, and subjected to agarose gel electrophoresis and electroelution to obtain an AatII-AvaI fragment (0.4 Kbp). Then, both ends of the AatII-AvaI fragment were made blunt ends with a blunting kit (Takara Shuzo Co., Ltd., Japan). The resulting fragment was ligated to SmaI site of pXBR 319 to obtain plasmid pXBRP 319.

(2) Plasmid pXBRP 319 obtained in above (1) was introduced into an excellent strain obtained by mutagenesis treatment of *Escherichia coli* IFO 14410 (obtained from Institute for Fermentation, Osaka, Japan) with NTG. The resulting strain was further subjected to mutagenesis with NTG to isolate various drug-resistant strains. A strain producing a large amount of biotin was selected from the drug-resistant strains to obtain *Escherichia coli* MM44/pXBRP 319 (FERM BP-4724).

(3) *Escherichia coli* MM44/pXBRP 319 obtained in above (2) was inoculated in 2×YT medium (20 ml) containing yeast extract 10 g/L, peptone 16 g/L and sodium chloride 5 g/L, and subjected to shaking culture at 37° C. for 16 hours. The resulting culture solution (0.2 ml) was transferred to 2×YT medium (20 ml), and subjected to shaking culture at 37° C. for 6 hours. The resulting culture was centrifuged, and the collected cells were rinsed twice with TM buffer (maleic acid 5.08 g/L, Tris 6.05 g/L, pH 6.0). The rinsed cells were suspended in TM buffer containing 200 µg/ml of NTG, and subjected to mutagenesis at 37° C. for 25 minutes. The treated cells were collected by centrifugation and rinsed twice with TM buffer, and suspended in the same buffer. The resulting suspension was inoculated in an agar plate of M9 minimal medium containing 1 mg/ml β-chloro-D-alanine, 4 µg/ml thiamine hydrochloride and 20 µg/ml Casamino acid, and allowed to stand at 37° C. for 5 days to obtain colonies of strains resistant to β-chloro-D-alanine. One of the strains was selected to obtain *Escherichia coli* BD10/pXBRP 319 (FERM BP-4725).

(4) *Escherichia coli* BD10/pXBRP 319 (FERM BP-4725) obtained in above (3) was subjected to mutagenesis with NTG, and various drug-resistant strains were selected. A strain producing a large amount of biotin was selected to obtain *Escherichia coli* MS10/pXBRP 319.

(5) *Escherichia coli* MS10/pXBRP 319 obtained in above (4) was inoculated in 2×YT medium (20 ml) containing yeast extract 10 g/L, peptone 16 g/L and sodium chloride 5 g/L, and subjected to shaking culture at 37° C. for 16 hours. The resulting culture solution (0.2 ml) was transferred to 2×YT medium (20 ml), and subjected to shaking culture at 37° C. for 6 hours. The resulting culture broth was centrifuged, and the collected cells were rinsed twice with TM buffer (maleic acid 5.08 g/L, Tris 6.05 g/L, pH 6.0). The rinsed cells were suspended in TM buffer containing 200 µg/ml of NTG, and subjected to mutagenesis at 37° C. for 25 minutes. The treated cells were collected by centrifugation and rinsed twice with TM buffer, and suspended in the same buffer. The resulting suspension was inoculated in an agar plate of M9 minimal medium containing 30 µg/ml 6-aminonicotinamide, 4 µg/ml thiamine hydrochloride and 20 µg/ml Casamino acid, and allowed to stand at 37° C. for 5 days to obtain colonies of strains resistant to 6-aminonicotinamide. One of the strains was selected and was designated as *Escherichia coli* ANA91/pXBRP319 (FERM BP-4928).

EXAMPLE 2

*Escherichia coli* ANA91/pXBRP319 obtained in Example 1 was grown at 37° C. for 16 hours in a 200 ml creased flask containing a seed medium (pH 7.1, 30 ml) composed of glucose 2%, calcium carbonate 1%, corn steep liquor 4%, ammonium sulfate 0.4%, $KH_2PO_4$ 0.1%, $K_2HPO_4$ 0.2% and $MgSO_4.7H_2O$ 0.01% on a rotary shaker. The resulting culture (0.6 ml) was transferred to a 200 ml creased flask containing a main medium (pH 7.1, 30 ml) composed of glucose 5%, corn steep liquor 5%, ammonium sulfate 0.2%, DL-alanine 0.3%, $KH_2PO_4$ 0.1%, $K_2HPO_4$ 0.2%, $MgSO_4.7H_2O$ 0.01%, $FeSO_4.7H_2O$ 0.001%, $MnSO_4.4–6H_2O$ 0.001% and thiamine hydrochloride 0.002%, and grown at 37° C. for 30 hours on a rotary shaker. After completion of the cultivation, the culture was centrifuged. The quantitative analysis of biotin in the culture supernatant showed that 160 mg/ml biotin was accumulated.

EXAMPLE 3

*Escherichia coli* ANA91/pXBRP319 obtained in Example 1 was grown at 37° C. for 16 hours in a 500 ml creased flask containing a seed medium (pH 7.1, 125 ml) composed of glucose 2%, calcium carbonate 1%, corn steep liquor 4%, ammonium sulfate 0.4%, $KH_2PO_4$ 0.1%, $K_2HPO_4$ 0.2% and $MgSO_4.7H_2O$ 0.01%, $FeSO_4.7H_2O$ 0.05%, thiamine hydrochloride 0.002% and tetracycline hydrochloride 0.0012% on a rotary shaker. The total amount of the culture thus obtained was transferred to a 5 liter jar fermentor containing a main medium (pH 7.1, 2.5 liters) composed of glucose 3%, corn steep liquor 6%, ammonium sulfate 0.2%, $KH_2PO_4$ 0.1%, $K_2HPO_4$ 0.2%, $MgSO_4.7H_2O$ 0.02%, DL-alanine 0.3%, $MnSO_4.4-6H_2O$ 0.003%, $FeSO_4.7H_2O$ 0.003%, $Fe_2(SO_4)_3.nH_2O$ 0.02%, thiamine hydrochloride 0.002%, 25% ammonia water 1.6 ml/liter and Actocoal (an antifoaming agent manufactured by Takeda Chemical Industries, Ltd.) 0.02%, and grown at 37° C. at an aeration rate of 2.5 liter/minute. The stirring number was increased from 550 to 850 rpm in proportion to the amount of the cells. An aqueous solution of glucose (66.7%) was continuously added so that the glucose. concentration was in the range of 0.1 to 0.5%.

During the cultivation, 25% ammonia water was added to maintain the pH in the range of 6.5 to 7.0. If necessary, Actocoal was added for antifoaming. The cultivation for 72 hours gave a culture containing biotin (550 mg/liter).

---

---

What is claimed is:

1. A microorganism resistant to 6-aminonicotinamide, which has a plasmid containing all or part of an *E. coli* biotin biosynthesis operon.

2. A process for producing biotin, which comprises culturing a microorganism according to claim 1 in a medium to produce and accumulate biotin in the medium, and collecting biotin.

3. An *E. coli* microorganism resistant to 6-aminonicotinamide, which has a plasmid containing all or part of an *E. coli* biotin biosynthesis operon.

4. A process for producing biotin, which comprises culturing a microorganism according to claim 3 in a medium to produce and accumulate biotin in the medium, and collecting biotin.

\* \* \* \* \*

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 114 bases
        ( B ) TYPE: nucleic acid
        ( C ) STRANDEDNESS: double
        ( D ) TOPOLOGY: linear ( i i ) MOLECULE TYPE: Genomic DNA ( i i i ) ORIGINAL SOURCE:
        ( A ) ORGANISM: Escherichia coli ( i v ) SEQUENCE DESCRIPTION: SEQ ID NO: 1:

```
CGTCCGTTGT  CATAATCGAC  TTGTAAACCA  AATTGAAAAG  ATTTAGGTTT        50

ACAAGTCTAC  ACCGAATTAA  CAACAAAAAA  CACGTTTTGG  AGAAGCCCCA       100

TGGCTCACCG  CCCA                                                 114
```